United States Patent
Wanda et al.

(10) Patent No.: US 10,828,010 B2
(45) Date of Patent: Nov. 10, 2020

(54) IMAGE DIAGNOSIS APPARATUS AND METHOD FOR DYNAMICALLY FOCUSING TRACKED ULTRASOUND PROBE WITH MULTIMODAL IMAGING SYSTEM

(71) Applicant: CANON KABUSHIKI KAISHA, Tokyo (JP)

(72) Inventors: Koichiro Wanda, Yokohama (JP); Takaaki Endo, Urayasu (JP); Kiyohide Satoh, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 472 days.

(21) Appl. No.: 15/398,045

(22) Filed: Jan. 4, 2017

(65) Prior Publication Data

US 2017/0112468 A1    Apr. 27, 2017

Related U.S. Application Data

(63) Continuation of application No. 12/871,634, filed on Aug. 30, 2010, now abandoned, which is a continuation of application No. PCT/JP2010/000606, filed on Feb. 2, 2010.

(30) Foreign Application Priority Data

May 1, 2009    (JP) .................................. 2009-112294

(51) Int. Cl.
*A61B 8/00*    (2006.01)
*A61B 5/055*    (2006.01)
*A61B 8/08*    (2006.01)

(52) U.S. Cl.
CPC ............ *A61B 8/4245* (2013.01); *A61B 5/055* (2013.01); *A61B 8/00* (2013.01); *A61B 8/42* (2013.01); *A61B 8/5238* (2013.01); *A61B 8/54* (2013.01)

(58) Field of Classification Search
CPC ........... A61B 8/4245; A61B 8/42; A61B 8/54; A61B 5/055; A61B 8/5238; A61B 8/00
See application file for complete search history.

(56) References Cited

U.S. PATENT DOCUMENTS

| 4,325,258 | A  | 4/1982 | Foster |
| 7,379,573 | B2 | 5/2008 | Tomoda et al. |

(Continued)

FOREIGN PATENT DOCUMENTS

| JP | 06-078922 A  | 3/1994 |
| JP | H11-113899 A | 4/1999 |

(Continued)

OTHER PUBLICATIONS

Beller et al (Feasibility of Navigated Resection of Liver Tumors Using; Ann Surg 2007;246: 288-294 (Year: 2007).*

(Continued)

*Primary Examiner* — Serkan Akar
(74) *Attorney, Agent, or Firm* — Carter, DeLuca & Farrell LLP

(57) ABSTRACT

This invention provides a technique to dynamically set an imaging parameter appropriate for observing a region of interest on an object to generate a high-quality echogram while maintaining the operability to change the position and orientation of a probe. A region-of-interest acquisition unit acquires region information that defines the region of interest. A position and orientation acquisition unit acquires position and orientation information representing the position and orientation of a probe. A parameter deciding unit obtains an imaging parameter based on the positional relationship between an imaging range decided based on the position and orientation information and the region of interest defined by the region information, and outputs the obtained imaging parameter to an imaging unit.

11 Claims, 9 Drawing Sheets

(56) References Cited

U.S. PATENT DOCUMENTS

| | | |
|---|---|---|
| 7,985,182 B2 | 7/2011 | Ichioka et al. |
| 9,396,576 B2 | 7/2016 | Miyasa et al. |
| 2002/0188193 A1* | 12/2002 | Biglieri .............. A61B 5/742 |
| | | 600/411 |
| 2004/0059214 A1 | 3/2004 | Tomoda et al. |
| 2004/0267128 A1 | 12/2004 | Matsumura |
| 2005/0090733 A1* | 4/2005 | Van Der Lugt ........ A61B 5/055 |
| | | 600/411 |
| 2005/0119569 A1 | 6/2005 | Ohtake |
| 2006/0184031 A1 | 8/2006 | Ichioka et al. |
| 2007/0078326 A1* | 4/2007 | Yoshikawa ............ A61B 8/08 |
| | | 600/407 |
| 2008/0009724 A1 | 1/2008 | Lee et al. |
| 2008/0089571 A1 | 4/2008 | Kurita |
| 2015/0070385 A1 | 3/2015 | Ishizu et al. |
| 2015/0235369 A1 | 8/2015 | Ishida et al. |
| 2016/0125584 A1 | 5/2016 | Suzuki et al. |
| 2016/0180526 A1 | 6/2016 | Satoh et al. |
| 2016/0180527 A1 | 6/2016 | Endo et al. |

FOREIGN PATENT DOCUMENTS

| | | | |
|---|---|---|---|
| JP | 2003-093389 A | 4/2003 | |
| JP | 2004-073379 A | 3/2004 | |
| JP | 2004-121652 A | 4/2004 | |
| JP | 2004-202260 A | 7/2004 | |
| JP | 2004-275223 A | 10/2004 | |
| JP | 2006-136441 A | 6/2006 | |
| JP | WO 2006059668 * | 6/2006 | ............... A61B 8/00 |
| JP | 2006-212445 A | 8/2006 | |
| JP | 2006-231035 A | 9/2006 | |
| JP | 2006-271523 A | 10/2006 | |
| JP | 2008-086742 A | 4/2008 | |
| JP | 2008-099729 A | 5/2008 | |
| JP | 2008-289732 A | 12/2008 | |
| WO | 2006-059668 A1 | 6/2006 | |
| WO | 2008/100623 A2 | 8/2008 | |

OTHER PUBLICATIONS

Office Action dated Feb. 22, 2013 in counterpart Japanese Application No. 2009-112294.

Office Action dated Jul. 11, 2014 in counterpart Japanese Application No. 2013-221514.

Gobbi et al., "2000 Ultrasound MRI Overlay with Image Warping for Neurosurgery", MICCAI 2000, LNCS 1935, pp. 106-114.

Solberg et al., "Freehand 3D ultrasound reconstruction algorithms—a review", Ultrasound in Medicine & Biology, vol. 33, No. 7, pp. 991-1009, Jul. 2007.

* cited by examiner

F I G. 12
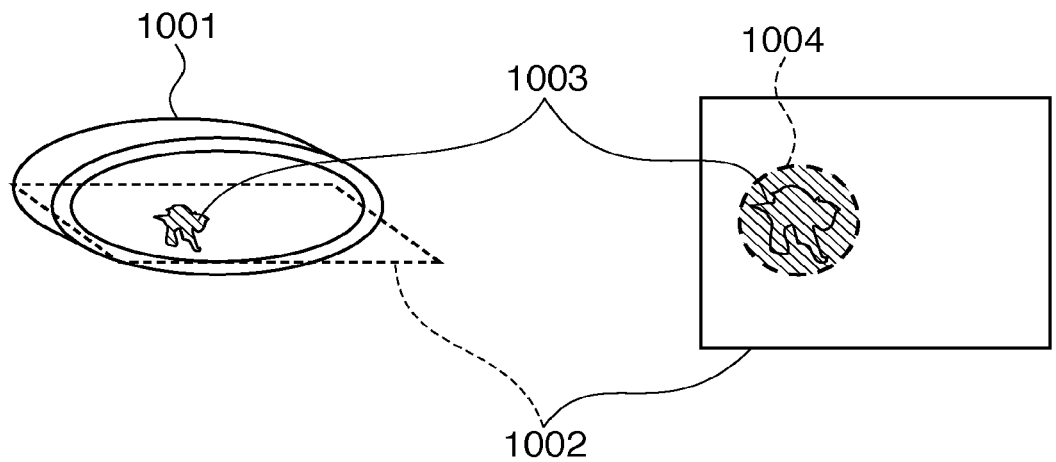
F I G. 13
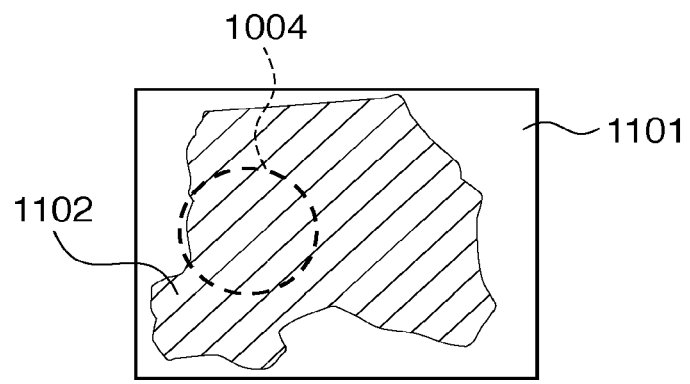
F I G. 14
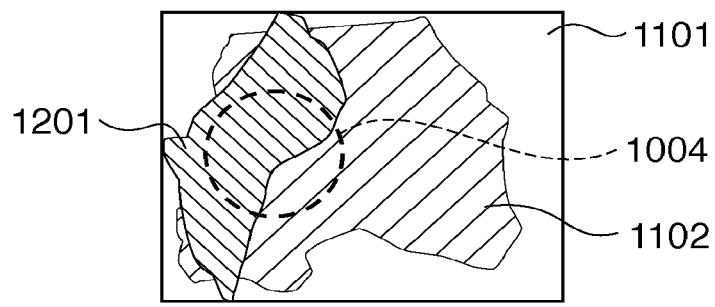

IMAGE DIAGNOSIS APPARATUS AND METHOD FOR DYNAMICALLY FOCUSING TRACKED ULTRASOUND PROBE WITH MULTIMODAL IMAGING SYSTEM

TECHNICAL FIELD

The present invention relates to an image diagnosis technique (modality) such as ultrasonic diagnosis.

BACKGROUND ART

An ultrasonic diagnosis apparatus transmits/receives ultrasonic waves to/from an object via an ultrasonic probe, generates tomograms and the like based on received signals, in other words, reflective echo signals including reflected waves and the like from the inside of the object, and provides information useful for diagnosis. The ultrasonic probe is generally formed by arranging a plurality of oscillators on a line, curve, or plane at equal intervals. A plurality of selected oscillators simultaneously oscillate to form an ultrasonic beam. The beam scans a part to be diagnosed in an object. Based on a reflective echo signal including a reflected wave of the beam or the like, an echogram which visualizes a slice of the object is generated.

To generate a high-quality echogram suitable for diagnosis in the medical field where the image diagnosis apparatus is used, various kinds of imaging parameters used to control the ultrasonic diagnosis apparatus need to be appropriately set in accordance with the observation target. An imaging parameter of the ultrasonic diagnosis apparatus is "STC (Sensitive Time Control)" which changes the gain of the amplifier of the receiving device in accordance with the reflective echo return time. "Depth" which controls the imaging range in the depth direction and "ultrasonic beam focus position" which controls focus processing are also known as adjustable imaging parameters. Sound pressure to be applied to an observation target is also adjusted.

As a focus processing method, for example, electronic focusing is known, which delays ultrasonic waves emitted from the simultaneously driven oscillators to make the wavefronts of the ultrasonic waves emitted from the oscillators match at an arbitrary focal point. The focus processing also includes a process to calculate the delay time of each received reflected wave and selectively receiving waves. For a linear probe, a depth position in the scanning line direction is the focus position.

In general, a doctor or technician interactively adjusts the imaging parameters using dials and levers provided on the console of the apparatus while visually confirming obtained images displayed on a monitor. However, several attempts to facilitate imaging parameter setting have also been reported.

For example, patent reference 1 discloses a method of designating a position of interest on an echogram acquired by ultrasonic beam transmission/reception, and performing focus processing for each scanning line to obtain a focus at the position of interest. Patent reference 2 discloses a method of designating a ROI (region of interest) on an echogram acquired by ultrasonic beam transmission/reception, and limiting the range to be scanned by an ultrasonic beam.

On the other hand, a technique is known which integrates two-dimensional echograms obtained freehand to generate a three-dimensional echogram (volume data) (three-dimensional reconstruction), and then generates an arbitrary cross section based on that volume data, thereby displaying an echogram more suitable for diagnosis (non-patent reference 1). According to this technique, for example, the same object is imaged using another image diagnosis apparatus (modality) such as an MRI to generate an echogram corresponding to a cross section of interest, and the obtained images are displayed side by side. This makes it possible to easily do diagnosis using a plurality of modalities. For example, patent reference 3 discloses a technique of detecting the position or movement of a probe and displaying the probe locus based on it, thereby indicating the presence/absence of an unscanned region.

CITATION LIST

Patent References

Patent Reference 1: Japanese Patent Laid-Open No. 2003-93389
Patent Reference 2: Japanese Patent Laid-Open No. 2008-99729
Patent Reference 3: Japanese Patent Laid-Open No. 2008-86742

Non-Patent References

Non-patent Reference 1: O. V. Solberg, F. Lindseth, H. Torp, R. E. Blake, and T. A. N. Hernes, "Freehand 3D ultrasound reconstruction algorithms—a review," Ultrasound in Medicine & Biology, vol. 33, no. 7, pp. 991-1009, July 2007.

SUMMARY OF INVENTION

Technical Problem

However, the conventional techniques can only designate a region of interest on an image. It is therefore impossible to appropriately apply the imaging parameters to a region outside the imaging range of the probe. In addition, the imaging parameters cannot appropriately be changed immediately following the position and orientation of the probe. When the probe has changed its position and orientation, the region of interest needs to be designated each time. Alternatively, the position and orientation of the probe must be fixed. That is, the use conditions are limited.

For example, when an object part (for example, cancerous tumor or specific organ) to be observed by a doctor with special interest is projected in a B-mode image, it is impossible to acquire an image always having a focus set on the part of interest while maintaining the operability to change the position and orientation of the probe.

The present invention has been made in consideration of the above-described problems, and has as its object to provide a technique to dynamically set an imaging parameter appropriate for observation of a region of interest on an object to generate a high-quality echogram while maintaining the operability to change the position and orientation of a probe.

Assume that the same object is imaged using another image diagnosis apparatus such as an MRI, and the image of the cross section of interest is compared with an echogram. In this case, to obtain the echogram corresponding to the cross section of interest, reconstruction of the three-dimensional echogram (volume data) of the entire target object is necessary. However, it is difficult to confirm whether the three-dimensional echogram necessary for generating the image of the cross section of interest has been generated.

To solve this problem, the technique disclosed in patent reference 3 implements a function of allowing to confirm whether the three-dimensional echogram of an entire target object has been acquired. However, it is impossible to determine whether imaging necessary for obtaining a specific cross section or part of interest to be observed by a doctor has been performed. For this reason, when generating a desired cross-sectional image or generating an image including a region of interest on a cross-sectional image, the image diagnosis apparatus needs redundant imaging processing and image processing, and the operator needs a redundant probe operation. It is therefore another object of the present invention to provide a technique of efficiently acquiring an image corresponding to a cross section or position of interest of another modality such as an MRI.

Solution to Problem

According to the present invention, there is provided an image diagnosis apparatus connected to an imaging apparatus for obtaining an image of an object, characterized by comprising first acquisition means for acquiring region information that defines a region of interest on the object, second acquisition means for acquiring position and orientation information representing a position and orientation of a probe provided in the imaging apparatus, calculation means for obtaining an imaging parameter of the imaging apparatus based on a positional relationship between an imaging range of the imaging apparatus decided based on the position and orientation information and the region of interest defined by the region information, and output means for outputting the imaging parameter.

Advantageous Effects of Invention

According to the arrangement of the present invention, it is possible to dynamically set an imaging parameter appropriate for observation of a region of interest on an object to generate a high-quality echogram while maintaining the operability to change the position and orientation of a probe. In addition, it is possible to efficiently acquire an image corresponding to a cross section or position of interest of another modality such as an MRI.

Further features of the present invention will become apparent from the following description of exemplary embodiments with reference to the attached drawings. Note that the same reference numerals denote the same or similar parts throughout the drawings.

BRIEF DESCRIPTION OF DRAWINGS

The accompanying drawings, which are incorporated in and constitute a part of the specification, illustrate embodiments of the invention and, together with the description, serve to explain the principles of the invention.

FIG. 12 is a view showing the relationship between volume data 1001, cross section 1002 of interest, morbid portion 1003, and partial region 1004 of interest of an MRI;

FIG. 13 is a view showing a display example of the echogram of the cross section of interest; and FIG. 14 is a view showing a display example of the echogram of the cross section of interest.

DESCRIPTION OF EMBODIMENTS

The embodiments of the present invention will now be described with reference to the accompanying drawings. Note that the embodiments to be explained below are examples of specifically practicing the present invention, and detailed embodiments described in the appended claims.

First Embodiment

An image diagnosis apparatus according to this embodiment is an ultrasonic diagnosis apparatus which images a region of interest by focus processing appropriate for imaging the region of interest defined on a reference coordinate system, and generates a three-dimensional echogram with a focus on the region of interest.

<Arrangement of Ultrasonic Diagnosis Apparatus of Embodiment>

Figure 1:
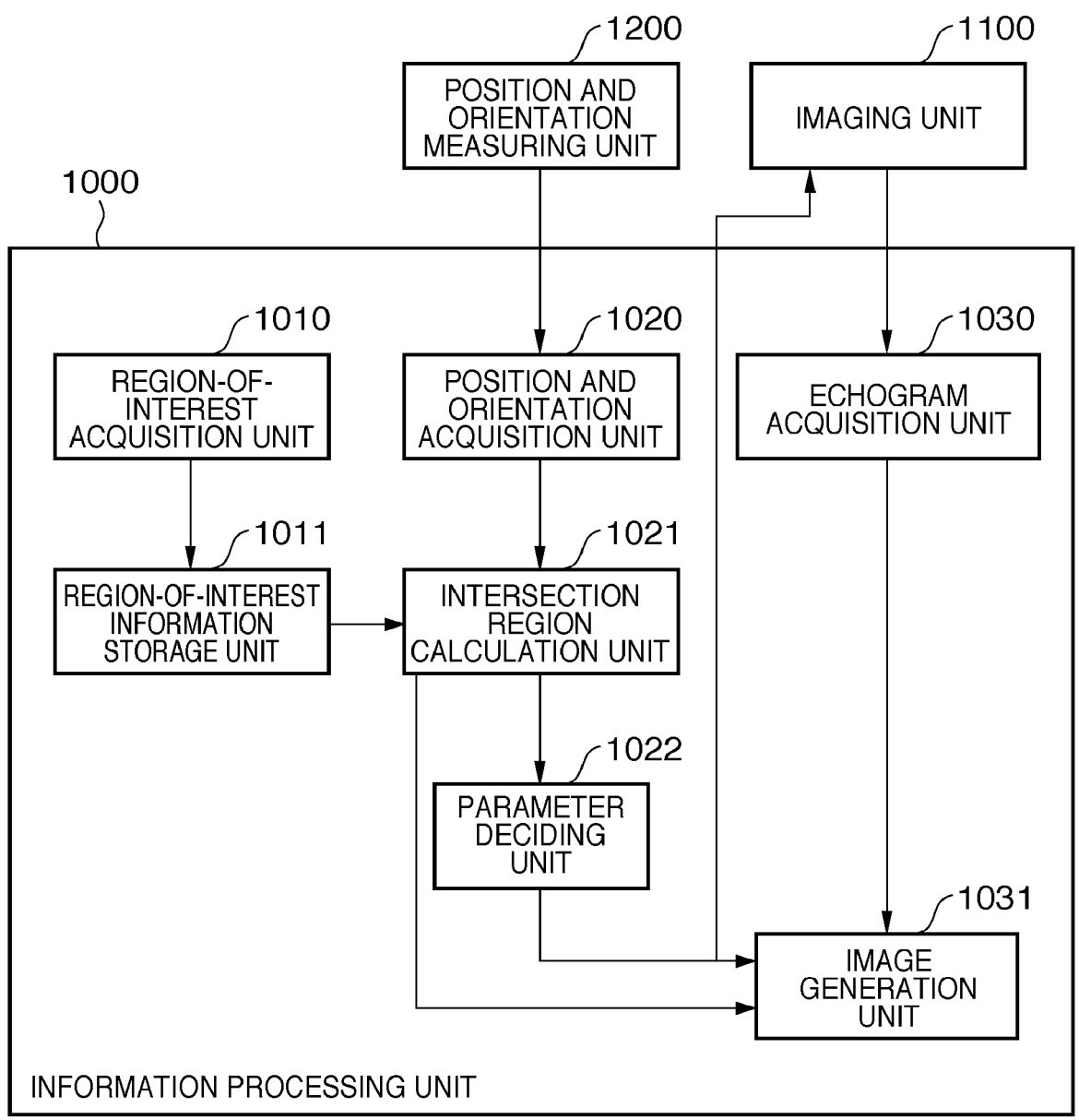
FIG. 1 is a block diagram showing an example of the functional arrangement of an ultrasonic diagnosis apparatus according to the first embodiment.

FIG. 1 is a block diagram showing an example of the functional arrangement of an ultrasonic diagnosis apparatus according to this embodiment. As shown in FIG. 1, the ultrasonic diagnosis apparatus according to this embodiment includes an information processing unit 1000, imaging unit 1100, and position and orientation measuring unit 1200.

The position and orientation measuring unit 1200 will be described first. The position and orientation measuring unit 1200 measures the position and orientation of an ultrasonic probe (not shown), which constitutes part of the imaging unit 1100, on a reference coordinate system defined in the physical space. The position and orientation measuring unit 1200 then transmits, to the information processing unit 1000, position and orientation information representing the measured position and orientation of the probe. As the position and orientation measuring unit 1200, a sensor of any type such as a magnetic sensor, mechanical sensor, or optical sensor is usable. Note that in the following explanation, the position and orientation measuring unit 1200 is assumed to be calibrated in advance so that the position and orientation information of the probe on the reference coordinate system can be acquired.

The reference coordinate system is, for example, a coordinate system whose origin is defined at one point in the physical space where the ultrasonic diagnosis apparatus of this embodiment is arranged (for example, an immobile point such as a bed on which a patient lies), and whose X-, Y-, and Z-axes are defined as three axes that cross at right angles at that origin. However, the following embodiment may be practiced using an object coordinate system (patient coordinate system) as the reference coordinate system by regarding an object (patient) as a rigid body. In this case, the position and orientation measuring unit 1200 also measures the position and orientation of the object. The position and orientation of the probe on the object coordinate system are calculated from the relative position and orientation relationship between the object and the probe. Note that the object coordinate system is a coordinate system whose origin is defined at one point on the object, and whose X-, Y-, and Z-axes are defined as three axes that cross at right angles at that origin.

The imaging unit 1100 (imaging apparatus) will be described next. The imaging unit 1100 obtains echograms of an object in accordance with an imaging parameter supplied from the information processing unit 1000. The echograms obtained by imaging are transmitted to the information processing unit 1000. Note that in this embodiment, the ultrasonic probe provided in the imaging unit 1100 is assumed to be of linear type, and an echogram imaged by the imaging unit 1100 is assumed to be a two-dimensional B-mode image. The imaging unit 1100 can have the same arrangement as that of a general ultrasonic diagnosis apparatus except that the imaging parameter can be controlled from the outside.

The information processing unit 1000 will be described next. The information processing unit 1000 obtains an imaging parameter appropriate for imaging a region of interest of an object, transmits the obtained imaging parameter to the imaging unit 1100, and sets it. In this embodiment, a focus position is used as the imaging parameter. In addition, the information processing unit 1000 acquires echograms from the imaging unit 1100 in which the imaging parameter is set, and integrates the acquired echograms, thereby generating a three-dimensional echogram associated with the region of interest.

As shown in FIG. 1, the information processing unit 1000 includes a region-of-interest acquisition unit 1010, region-of-interest information storage unit 1011, position and orientation acquisition unit 1020, intersection region calculation unit 1021, parameter deciding unit 1022, echogram acquisition unit 1030, and image generation unit 1031.

The region-of-interest acquisition unit 1010 acquires region information which defines a region of interest of an object in the physical space (in the reference coordinate system) (first acquisition). The region information can be of any type as far as it can define a region of interest of an object in the physical space. For example, information representing the three-dimensional coordinate values of the central position of a region and the radius of the region is usable. Alternatively, formula information to be used to derive it may be used. In this embodiment, a region of interest is assumed to be a sphere, and region information is assumed to be information representing the three-dimensional coordinate values of the center of the sphere and the radius of the sphere. Note that the input form of region information to the information processing unit 1000 is not particularly limited. The region information may be received from an external apparatus via a network, or input from a keyboard, mouse, or the like operated by the user. The region-of-interest acquisition unit 1010 acquires region information input in this way, and temporarily stores it in the region-of-interest information storage unit 1011.

The position and orientation acquisition unit 1020 acquires, from the position and orientation measuring unit 1200, position and orientation information representing the position and orientation of the probe of the imaging unit 1100 on the reference coordinate system (second acquisition). The position and orientation acquisition unit 1020 sends the acquired position and orientation information to the intersection region calculation unit 1021 of the succeeding stage.

The intersection region calculation unit 1021 performs the following processing using the region information stored in the region-of-interest information storage unit 1011 and the position and orientation information sent from the position and orientation acquisition unit 1020. More specifically, the intersection region calculation unit 1021 obtains, as an intersection region, a cross section of the region of interest defined by the region information in the imaging range of the imaging unit 1100 which is decided based on the position and orientation information. The intersection region calculation unit 1021 sends information (intersection region information) representing the thus obtained intersection region to the parameter deciding unit 1022 of the succeeding stage. The intersection region calculation unit 1021 also sends the region information and position and orientation information to the image generation unit 1031 of the succeeding stage.

The parameter deciding unit 1022 calculates an optimum imaging parameter to be set in the imaging unit 1100 using the intersection region information sent from the intersection region calculation unit 1021. In this embodiment, the parameter deciding unit 1022 calculates a focus position at which an in-focus state is obtained in a region on the object corresponding to the intersection region. The parameter deciding unit 1022 transmits the calculated imaging parameter to the imaging unit 1100. The parameter deciding unit 1022 also sends, to the image generation unit 1031 of the succeeding stage, the obtained imaging parameter and the intersection region information used to obtain the imaging parameter.

The echogram acquisition unit 1030 acquires an echogram obtained by the imaging unit 1100. Note that the acquired echogram is associated with the imaging parameter obtained by the parameter deciding unit 1022 and various kinds of information used to obtain the imaging parameter. For example, the imaging parameter and various kinds of information used by the parameter deciding unit 1022 are added with the same identifier. This identifier is also added to the obtained echogram, thereby associating them. If an imaging parameter is uniquely decided in correspondence with each position and orientation of the probe, the position and orientation information of the probe may be used as identification information. Alternatively, various kinds of information used by the parameter deciding unit 1022 may be transmitted to the imaging unit 1100 together with the imaging parameter, added to the echogram, and then input to the echogram acquisition unit 1030 again.

The image generation unit 1031 integrates echograms acquired by the echogram acquisition unit 1030 to generate a three-dimensional echogram (volume data) including the region of interest. The image generation unit 1031 outputs the generated three-dimensional echogram. The output destination is not particularly limited. The three-dimensional echogram may be transmitted to an external apparatus via a network, or output to a display apparatus for the purpose of display.

<Processing Procedure to be Performed by Ultrasonic Diagnosis Apparatus>

Figure 3:
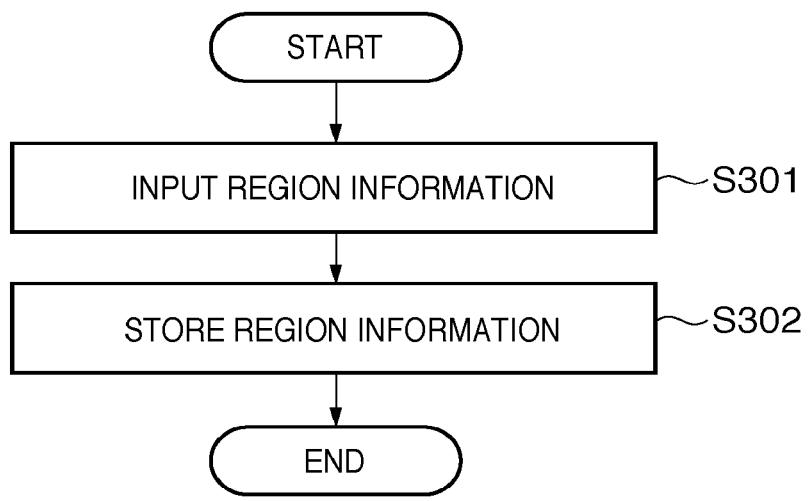
FIG. 3 is a flowchart of processing to be executed by a region-of-interest acquisition unit 1010.

Processing to be performed by the ultrasonic diagnosis apparatus according to the embodiment will be described next. FIG. 3 is a flowchart of processing to be executed by the region-of-interest acquisition unit 1010. In step S301, the region-of-interest acquisition unit 1010 acquires region information that defines a region of interest of an object in the physical space (in the reference coordinate system). In step S302, the region-of-interest acquisition unit 1010 temporarily stores the acquired region information in the region-of-interest information storage unit 1011.

Figure 4:
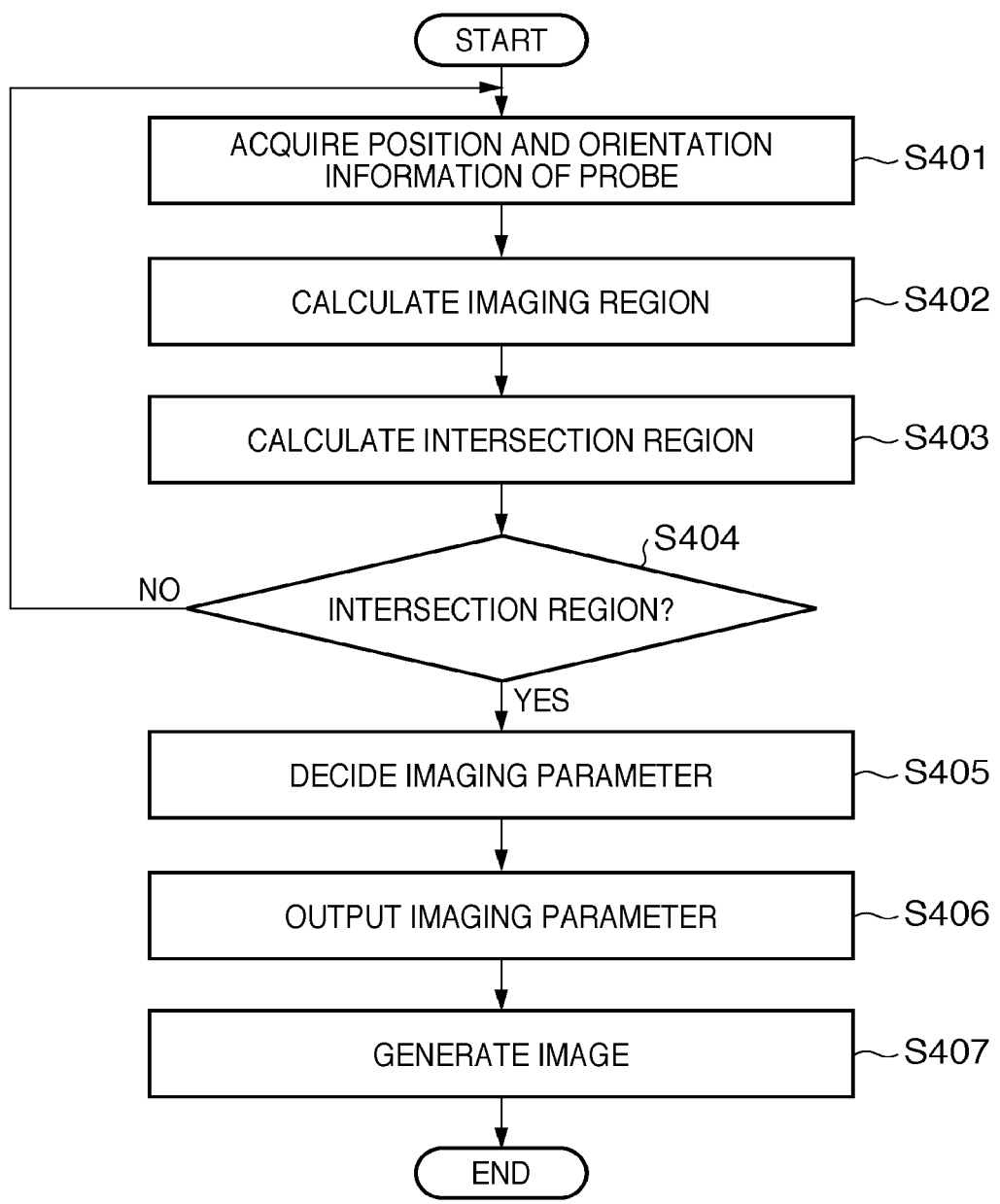
FIG. 4 is a flowchart of processing of generating a three-dimensional echogram including a region of interest.

Processing of generating a three-dimensional echogram including a region of interest will be described below with reference to FIG. 4 which shows the flowchart of the processing. Note that processing according to the flowchart of FIG. 4 is executed after processing according to the flowchart of FIG. 3 has ended. When the processing according to the flowchart of FIG. 4 starts, the ultrasonic diagnosis apparatus has already been activated so as to be able to obtain an echogram, and the position and orientation of the probe have also been measured.

In step S401, the position and orientation acquisition unit 1020 acquires the position and orientation information of the probe from the position and orientation measuring unit 1200, and sends the acquired position and orientation information to the intersection region calculation unit 1021 of the succeeding stage. In step S402, the intersection region calculation unit 1021 calculates information (imaging region information) representing the imaging region (imaging range) of the probe on the reference coordinate system using the position and orientation information of the probe. The imaging region is information representing a region in the physical space, which is captured in an image to be obtained by the probe. The imaging region is defined by a plane (imaging plane) in the physical space and a region on the plane. The imaging plane is uniquely defined in the reference coordinate system based on the position and orientation of the probe. On the other hand, the region on the plane is calculated based on the number of oscillators, the pitch between the oscillators, the depth in the direction of echo signal transmission, and the like. Note that the number of oscillators, the pitch between them, and the model of beam forming are assumed to be known information.

In step S403, the intersection region calculation unit 1021 obtains a cross section of the region of interest in the imaging region as an intersection region using the region information stored in the region-of-interest information storage unit 1011 and the imaging region information calculated in step S402. In this embodiment, since the region of interest is expressed as a sphere, the calculated intersection region is described by a circle (center coordinates and radius) on an echogram. Note that the parameters of a circle on a plane obtained by cutting a sphere in a space along the plane can be derived using rudimentary geometry, and a detailed description thereof will be omitted here.

Figure 5:
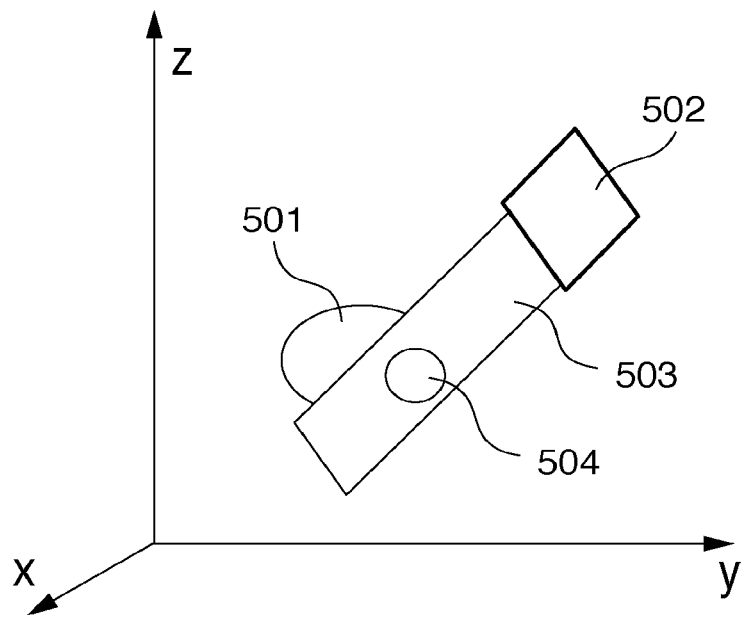
FIG. 5 is a view showing examples of a region of interest, a probe imaging region, and an intersection region between them on a reference coordinate system.

FIG. 5 is a view showing examples of a region of interest, a probe imaging region, and an intersection region between them on the reference coordinate system. Referring to FIG. 5, reference numeral 501 denotes a region of interest (sphere); 502, a probe; 503, an imaging region calculated based on the position and orientation information of the probe; and 504, a circle (intersection region) representing a cross section of the region 501 of interest in the imaging region 503. Note that a portion of the region 501 of interest shown in FIG. 5 on the near side of the intersection region 504 is not illustrated for the descriptive convenience.

The intersection region calculation unit 1021 sends information (intersection region information) of the thus obtained intersection region to the parameter deciding unit 1022 of the succeeding stage. The intersection region calculation unit 1021 also sends the region information and the position and orientation information to the image generation unit 1031 of the succeeding stage.

In step S404, the intersection region calculation unit 1021 determines whether the intersection region could be obtained in step S403. Upon determining that the intersection region could not be obtained, the process returns to step S401, and the processes in steps S401 to S403 are repeated based on the position and orientation information of the probe input at the next time. On the other hand, if the intersection region could be obtained, the process advances to step S405.

Figure 6:
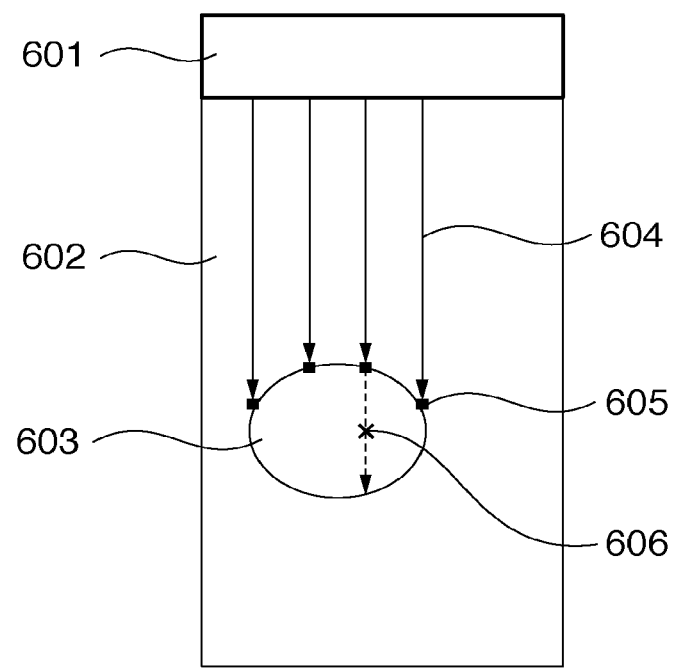
FIG. 6 is a schematic view showing the relationship between a probe 601, an imaging region 602, and an intersection region 603 when viewed from a direction perpendicular to a plane serving as the imaging region.

In step S405, the parameter deciding unit 1022 obtains an imaging parameter based on the intersection region information. FIG. 6 is a schematic view showing the relationship between a probe 601, an imaging region 602, and an intersection region 603 when viewed from a direction perpendicular to a plane serving as the imaging region. Referring to FIG. 6, the intersection region 603 can be recognized as a region on the plane representing the imaging region 602.

Various methods are available to decide a focus position 605. In this embodiment, the user may select one of the methods, or a predetermined deciding method may be used. For example, to set a focus near the boundary of the intersection region 603, the distance up to the intersection region 603 is decided as the focus position 605 independently for each scanning line 604. To set a focus inside the intersection region 603, an intermediate position between the intersections (two points) of the scanning line 604 and the intersection region 603 may be set as the focus position, as indicated by 606. Alternatively, the distance up to the central point of the intersection region 603 may be set as the focus position common to all scanning lines. Any other deciding method capable of setting a focus on the intersection region 603 is usable. For example, a focus position deciding method disclosed in patent reference 1 is also applicable.

In step S406, the parameter deciding unit 1022 sends the obtained imaging parameter to the imaging unit 1100. This allows the imaging unit 1100 to set, in itself, the imaging parameter obtained by the parameter deciding unit 1022 and obtain an echogram in accordance with the set imaging parameter. The imaging unit 1100 transmits the obtained echogram to the information processing unit 1000. The parameter deciding unit 1022 also sends the obtained imaging parameter and the intersection region information used to obtain the imaging parameter to the image generation unit 1031 of the succeeding stage.

In step S406, the echogram acquisition unit 1030 acquires the echogram transmitted from the imaging unit 1100, and sends it to the image generation unit 1031 of the succeeding stage. In step S407, the image generation unit 1031 accumulates echograms sent from the echogram acquisition unit 1030 in the internal memory (not shown) of the information processing unit 1000. At this time, each echogram is associated with the imaging parameter obtained by the parameter deciding unit 1022 or various kinds of information used to obtain the imaging parameter, as described above.

The image generation unit 1031 generates a three-dimensional echogram (volume data) by performing three-dimensional reconstruction processing using the position and orientation information of the probe and all echograms stored until this point of time. The three-dimensional reconstruction processing can be done using any method if the processing can reconstruct a three-dimensional volume from a plurality of echograms. For example, a method described in the following reference is usable.

A. Fenster, "3-Dimensional Ultrasound Imaging," Imaging Economics, 2004.

The above-described processes in steps S401 to S407 are repeated in accordance with the echogram transmission rate of the imaging unit 1100. When the user changes the position and orientation of the probe by the same operation as in normal diagnosis, echogram imaging is repeated, and an imaging parameter appropriate for imaging the region of interest is set independently of the position and orientation of the probe (that is, focus processing is always performed for the region of interest). Integrating the images enables to generate a three-dimensional echogram having a focus on the region of interest.

Note that in this embodiment, the information processing unit 1000 and the imaging unit 1100 are separate devices. However, they may be put together into one device. The system arrangement is not particularly limited if it can implement the above-described functions of the embodiment. For example, it is also possible to practice a system which forms the information processing unit 1000 in a three-dimensional medical imaging apparatus such as an MRI, and controls the imaging parameter of the ultrasonic diagnosis apparatus.

As described above, according to this embodiment, it is possible to apply an imaging parameter appropriate for observing a part of interest on an object. In addition, even if the position and orientation of the probe change, the imaging parameter is appropriately changed immediately following the position and orientation of the probe. This saves re-designating the region of interest. It is therefore possible to observe the part of interest without degrading the operability for the user.

Furthermore, the region of interest can be designated before imaging. The region of interest can also be designated based on another three-dimensional image data. When a plurality of images (each image partially includes the region of interest) obtained based on the imaging parameter appropriate for observing the region of interest are integrated, a high-quality image of the entire region of interest can be obtained.

Several modifications will be explained below. These modifications should not simply be regarded as modifications of only the first embodiment but should be recognized as modifications of the second or subsequent embodiment or modifications for a combination of several embodiments.

<First Modification>

In the first embodiment, the region of interest is expressed as a sphere. However, the method of expressing the region of interest is not limited to this. Additionally, the region-of-interest acquisition unit 1010 acquires the region information of the region of interest in various forms, as described in the first embodiment, and the acquisition method is not limited to a specific one.

For example, the region information of the region of interest may be acquired from a three-dimensional medical image obtained by another modality such as an MRI or PET. In this case, the region of a part of interest in the three-dimensional medical image may be extracted semi-automatically or manually as the region information of the region of interest. Examples of the region of interest are a region being suspected to include a cancerous tumor in volume data obtained by an MRI, and a three-dimensional region such as a segmented organ.

The region information of the region of interest is described as, for example, labeled volume data (a set of three-dimensional point groups). Alternatively, the obtained region may be approximated by a sphere or a rectangle or more simply described using only three-dimensional coordinates representing the position of the part of interest (central position or position of center of gravity). A result of segmentation may be described by a function (for example, implicit polynomial). The region-of-interest acquisition unit 1010 acquires the region information of the region of interest from an apparatus for performing the segmentation or an apparatus which holds the result. Based on the thus obtained region information, the user may perform an operation of enlarging or reducing the region of interest via an input device such as a mouse or a keyboard.

Note that alignment between the three-dimensional medical image and the reference coordinate system is assumed to have already been done by another means (that is, coordinate transformation from the coordinate system of the three-dimensional medical image to the reference coordinate system is assumed to be possible). The region of interest may two-dimensionally be designated on an echogram, and converted into the region information of the region of interest on the reference coordinate system based on the position and orientation information of the probe.

<Second Modification>

In the first embodiment, the region of interest has been described as three-dimensional shape data. However, an arbitrary cross section in three-dimensional shape data of another medical imaging apparatus (for example, MRI) may be designated as a region of interest.

In this case, in step S301, three-dimensional shape data from an MRI is displayed on a GUI by volume rendering, and a cross section on the three-dimensional shape data from an MRI is designated by an operation using a mouse or a keyboard. The cross section is converted into a plane on the reference coordinate system by coordinate transformation. In step S403, the intersection region 504 is acquired as the line of intersection between the plane of interest and a plane representing the imaging region of the probe. In step S405, a focus is set for each scanning line to the line of intersection. In step S407, each pixel value on the line of intersection of an echogram obtained by the imaging unit 1100 may be projected as a pixel value on the plane of interest, thereby generating a two-dimensional echogram corresponding to the designated arbitrary cross section from an MRI. That is, according to this modification, it is possible to acquire a high-quality echogram in the same region as a cross section in three-dimensional shape data of a medical imaging apparatus such as an MRI.

<Third Modification>

In the first embodiment, the imaging parameter is obtained using the intersection region between the imaging region and the region (region of interest) represented by region information. However, any other method is also usable if it defines the imaging parameter based on the positional relationship between the probe and the region of interest (the positional relationship between an imaging range determined based on the position and orientation information of the probe and the region represented by region information).

For example, even when no intersection region exists between the imaging region and the region of interest, one point in the imaging region closest to the region of interest may be selected, and the distance up to the point may be set as a focus value. For example, when the region of interest is designated by a point, intersection with the imaging region rarely occurs. For this reason, the coordinate value of the foot of a perpendicular from the point of interest to the imaging plane is set as a focus position. More simply, the depth-direction coordinate value of the point of center of gravity of the region of interest on the probe coordinate system may be set as a focus position.

<Fourth Modification>

In the first embodiment, the imaging parameter is a focus position. However, any other type of parameter is also usable. For example, STC, depth, focusing range, or sound pressure may be adjusted.

For example, to adjust the focusing range, the imaging parameter is adjusted in step S406 such that the line of intersection between the scanning line 604 and the intersection region 603 falls within the focusing range. To adjust the depth, the intersection region between the imaging plane (a plane including the imaging region) and the region of interest is calculated, and the depth is adjusted such that the intersection region is included in the imaging region. To adjust sound pressure, the magnitude of sound pressure is adjusted in accordance with the position of center of gravity of the target region (if the position of center of gravity is far, the sound pressure is increased, and if the position of center of gravity is close, the sound pressure is reduced). Only one of these parameters may be adjusted, or a plurality of parameters may be adjusted.

<Fifth Modification>

In the first embodiment, echograms acquired by the imaging unit 1100 are composited to generate a three-dimensional echogram. However, this arrangement is not always necessary. For example, the arrangement may only control the imaging parameter of the imaging unit 1100. In this case, it is necessary to only display an image obtained by the imaging unit 1100 on a display device such as a monitor.

<Sixth Modification>

In the first embodiment, an echogram is obtained using a one-dimensional array probe for acquiring a two-dimensional image. However, the effects described in the first embodiment can be obtained even using a two-dimensional array probe for acquiring a three-dimensional image, as a matter of course. In this case, the intersection region between the region of interest and the imaging region is a three-dimensional region on the reference coordinate system.

<Seventh Modification>

Instead of generating three-dimensional volume data using the whole of an acquired echogram, three-dimensional reconstruction of only the region of interest may be done using only the information of the region of interest. In this case, when each pixel value of the region of interest is to be decided from a pixel value of the intersection region 603, only several pixels of the intersection region 603 where imaging is expected to be done satisfactorily may be acquired as the pixel values of the region of interest.

For example, a focusing range having a fixed length is set. Out of line segments where the scanning lines 604 overlap the intersection region 603, only pixels on line segments within the focusing range may be acquired as the pixel values of the region of interest. At this time, of the region information stored in the region-of-interest information storage unit 1011, a region where the pixel values of an echogram within the focusing range have been acquired in the region of interest and a region where the pixel values have not been acquired yet may be made identifiable. When the processes in steps S401 to S408 are repeated for the region where the pixel values have not been acquired yet in the region of interest to generate an echogram of the region of interest formed from only pixels within a specific focusing range, the whole region of interest can be generated using the pixel values of the echogram within the focusing range. To identify the region where the pixel values have not been acquired, for example, a flag may be set for coordinates, each voxel of volume data, or each pixel on a plane or a line. Alternatively, another information representing the region where the pixel values have not been acquired may be added.

<Eighth Modification>

In step S406, the imaging parameter may be decided in consideration of not only the positional relationship between the region of interest and the probe on the reference coordinate system but also attenuation of an ultrasonic wave in the living body. For example, the FDA (Frequency Dependent Attenuation) of the living body through which an ultrasonic wave propagates can be specified using the positional relationship between the region of interest and the probe on the reference coordinate system (for example, skin, breast, and organ). The attenuation amount of an ultrasonic echo can be calculated for each ultrasonic frequency. The attenuation amount of the intensity of an ultrasonic wave that enters the region of interest and is reflected by it may be calculated for each position and orientation of the probe. An imaging parameter may then be decided, which unifies the intensity of the ultrasonic wave transmitted to each point of the region of interest or the intensity of the received ultrasonic wave.

<Ninth Modification>

In step S406, if the intersection region 603 between the imaging region of the probe and the region of interest is included in the imaging region 602, the direction of each scanning line may be controlled such that the scanning lines 604 which do not overlap the intersection region 603 can strike the region of interest. That is, the imaging parameter may be decided such that the directions of the scanning lines 604 change so as to make all scanning lines of the probe overlap the intersection region 603. To change the direction of a scanning line of the probe, the time delay of the oscillators of the probe may be changed, or any other method is also usable.

Second Embodiment

In this embodiment, the method of obtaining an intersection region in accordance with the expression form (for example, sphere, rectangular parallelepiped, or point) of a region of interest is changed. Note that from this embodiment, only points different from the already described embodiment will be explained. The remaining points are assumed to be the same as in the already described embodiment unless it is specifically stated otherwise.

<Arrangement of Ultrasonic Diagnosis Apparatus of Embodiment>

Figure 7:
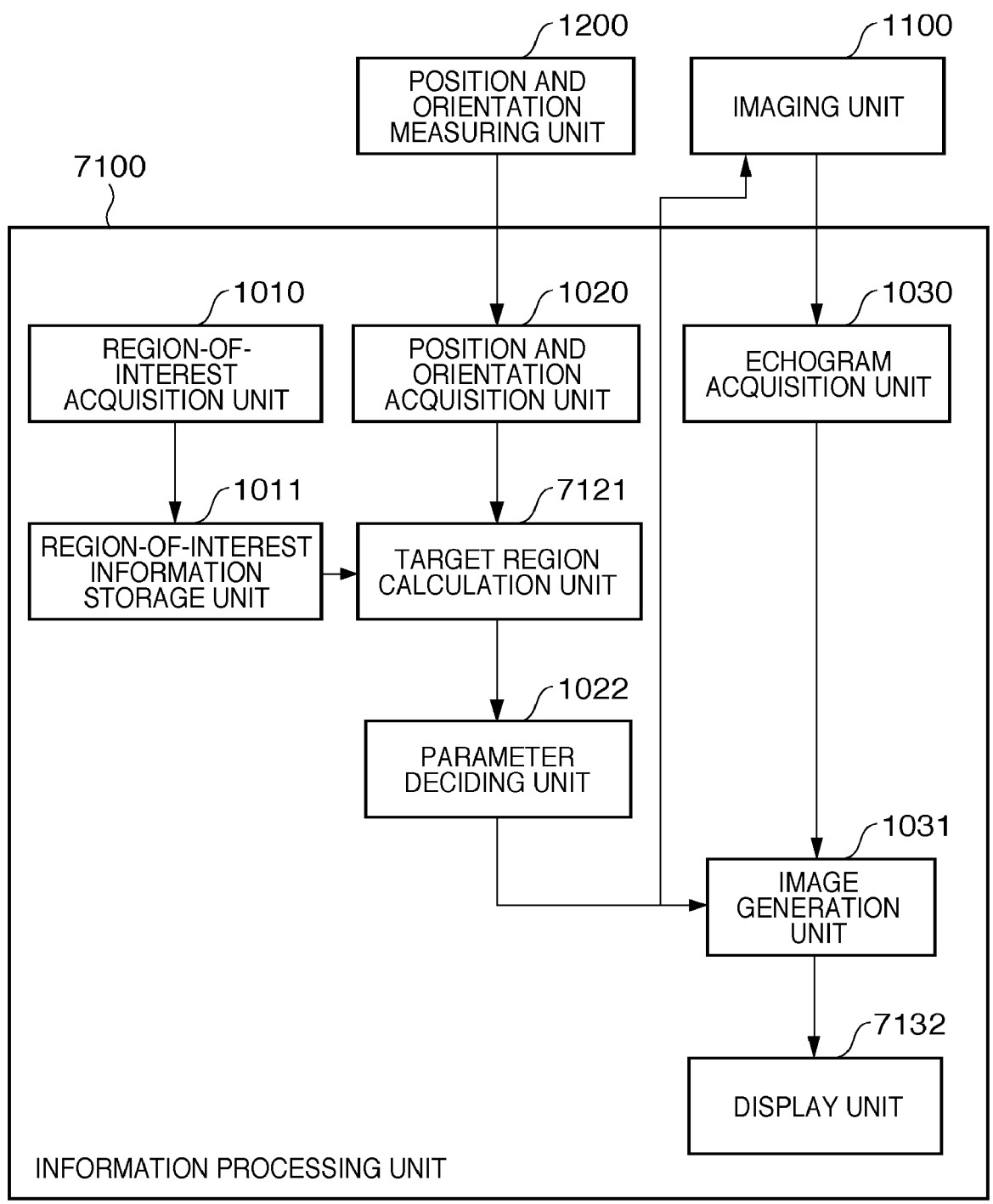
FIG. 7 is a block diagram showing an example of the functional arrangement of an ultrasonic diagnosis apparatus according to the second embodiment of the present invention.

FIG. 7 is a block diagram showing an example of the functional arrangement of an ultrasonic diagnosis apparatus according to this embodiment. As shown in FIG. 7, the ultrasonic diagnosis apparatus according to this embodiment includes an information processing unit 7100, imaging unit 1100, and position and orientation measuring unit 1200. That is, the components other than the information processing unit 7100 are the same as in the first embodiment. Hence, the information processing unit 7100 will be described below.

As shown in FIG. 7, the information processing unit 7100 includes a region-of-interest acquisition unit 1010, regionof-interest information storage unit 1011, position and orientation acquisition unit 1020, target region calculation unit 7121, parameter deciding unit 1022, echogram acquisition unit 1030, and display unit 7132. That is, the components other than the target region calculation unit 7121 and the display unit 7132 are the same as in FIG. 1, and a description thereof is also the same as in the first embodiment. The target region calculation unit 7121 and the display unit 7132 will mainly be explained below.

In this embodiment as well, the region-of-interest acquisition unit 1010 acquires region information. Various expression forms are usable for the region information, as described in the first embodiment. For example, if the region of interest is a point (point of interest), the three-dimensional coordinates of the point of interest on the reference coordinate system are acquired as region information. Alternatively, a region of interest having a three-dimensional shape may be described using another shape such as a rectangular parallelepiped or a polyhedron.

The region information may be described as labeled volume data (three-dimensional point group). Alternatively, a point group representing the region of interest may be approximated by a polyhedron or a polynomial. These expression methods are especially effective when a part of interest such as a tumor is extracted, as a region of interest, from a three-dimensional medical image obtained in advance by another modality such as an MRI (Magnetic Resonance Imager). In this case, preferably, the user designates a file or the like containing region information on an MRI or an image server connected to the ultrasonic diagnosis apparatus via a network, and the region-of-interest acquisition unit 1010 reads it out.

Note that when using data of another modality, alignment of the data to the reference coordinate system is assumed to have already been done by another means. That is, coordinate transformation of the data to the reference coordinate system has already been done. Alternatively, a coordinate system that defines the image of the modality may be used as the reference coordinate system.

Using region information stored in the region-of-interest information storage unit 1011 and position and orientation information sent from the position and orientation acquisition unit 1020, the target region calculation unit 7121 performs processing of obtaining a region to be used to obtain an imaging parameter as a target region. The target region calculation unit 7121 sends information (target region information) representing the thus obtained target region to the parameter deciding unit 1022 of the succeeding stage. The target region calculation unit 7121 also sends the region information and the position and orientation information to the image generation unit 1031 of the succeeding stage.

The display unit 7132 can display an echogram generated by the image generation unit 1031 or display a GUI (Graphical User Interface) for the user. Note that image generation by the image generation unit 1031 and image display by the display unit 7132 can be executed for every imaging by the imaging unit 1100 or for a predetermined number of times of imaging or imaging in a predetermined time. This is set by an instruction input by the user.

<Processing Procedure to be Performed by Ultrasonic Diagnosis Apparatus>

Processing to be performed by the ultrasonic diagnosis apparatus according to the embodiment will be described next. Processing to be executed by the region-of-interest acquisition unit 1010 is the same as in the first embodiment. This processing is performed in accordance with the flowchart shown in FIG. 3. However, the second embodiment allows input of region information in various expression forms.

If the region of interest is a sphere, the region information represents the three-dimensional coordinate values of the sphere and the radius of the sphere, as in the first embodiment. If the region of interest is a rectangular parallelepiped or a polyhedron, the region information represents the coordinates of each vertex or equations representing the position and region of the parallelepiped or polyhedron. If the region of interest is a point (point of interest), the region information represents the coordinates of the point of interest. If the region of interest is labeled volume data, the region information may represent either a point group or equations or information representing the position and shape of the volume data.

That is, this embodiment allows input of region information in various forms. The region-of-interest acquisition unit 1010 may acquire a file in which such region information is described by reading out the file, as a matter of course. The region information is temporarily stored in the region-of-interest information storage unit 1011.

Processing of generating a three-dimensional echogram including a target region will be described below with reference to FIG. 8 which shows the flowchart of the processing. Note that the same step numbers as in FIG. 4 indicate steps of performing the same processes in FIG. 8, and a description thereof will not be repeated.

Figure 8:
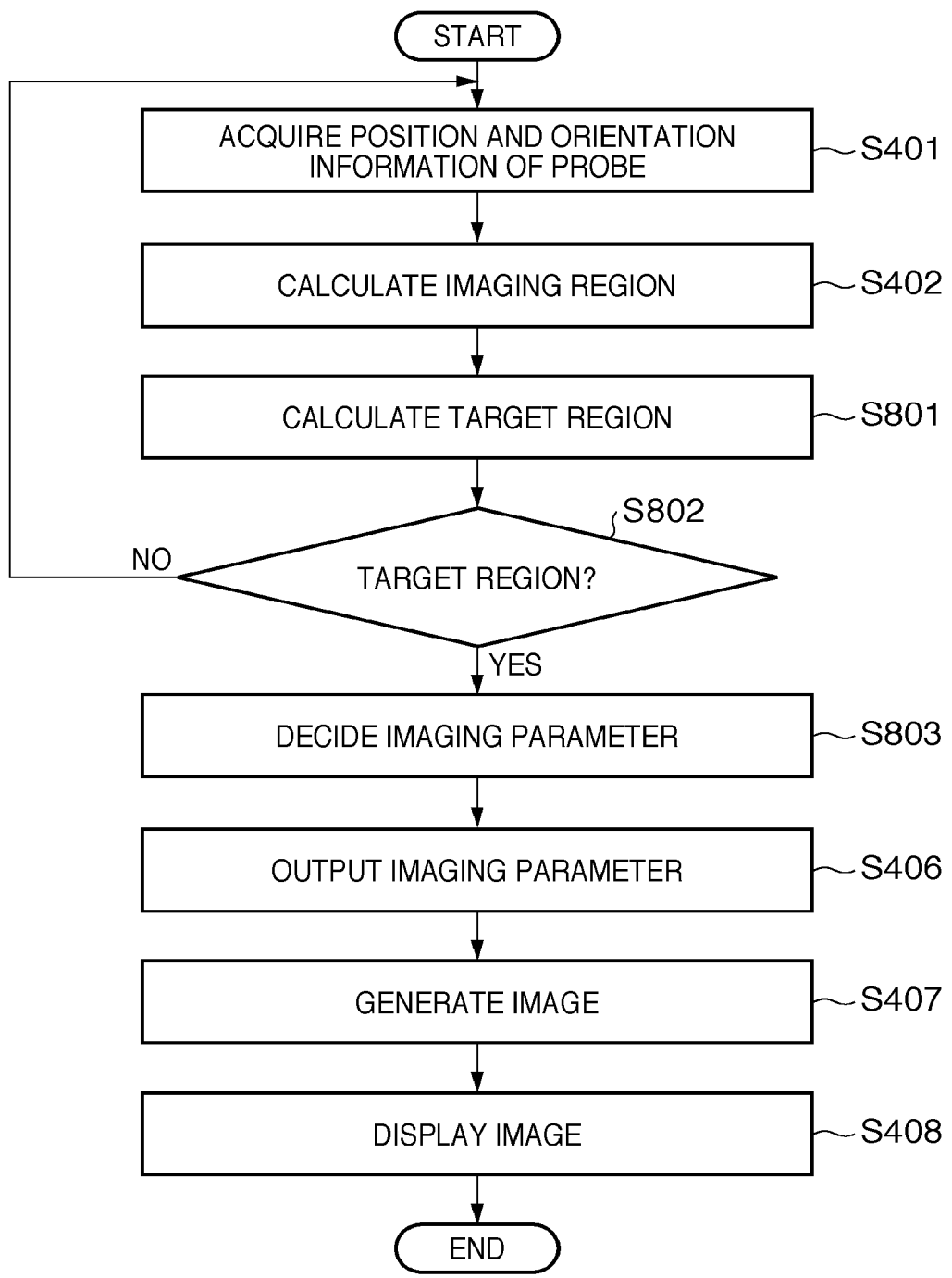
FIG. 8 is a flowchart of processing of generating a three-dimensional echogram including a target region.

Note that processing according to the flowchart of FIG. 8 is executed after processing according to the flowchart of FIG. 3 has ended. When the processing according to the flowchart of FIG. 8 starts, the ultrasonic diagnosis apparatus has already been activated so as to be able to obtain an echogram, and the position and orientation of the probe have also been measured.

In step S801, the target region calculation unit 7121 obtains a target region to be used to obtain an imaging parameter, using the region information stored in the region-of-interest information storage unit 1011 and the imaging region information calculated in step S402. The target region calculation unit 7121 selects a predetermined appropriate method in accordance with the expression form of the region of interest, and calculates the target region using the selected method.

More specifically, when the region of interest is expressed as a sphere, rectangular parallelepiped, polyhedron, or labeled volume data, the intersection region between the region of interest and the imaging region is calculated as the target region. On the other hand, if the region of interest is expressed as a point, a neighboring region is calculated as the target region. Note that the association between the expression form of the region of interest and a corresponding target region calculation method is assumed to be done in advance and managed by the target region calculation unit 7121.

For example, when the region of interest is a sphere, the target region calculation unit 7121 calculates, as the target region, the intersection region between the region of interest and the imaging region, as in the first embodiment. For example, when the region of interest is a rectangular parallelepiped, the target region calculation unit 7121 calculates, as the target region, the intersection region between the region of interest and the imaging region, as in the case of the sphere. More specifically, a polygonal region formed from the lines of intersection between the respective planes of the rectangular parallelepiped and a plane representing the imaging region is calculated as the target region.

For example, when the region of interest is a polyhedron, the target region calculation unit 7121 calculates, as the target region, the intersection region between the region of interest and the imaging region, as in the case of the sphere. More specifically, a polygonal region formed from the lines of intersection between all planes of the polyhedron and a plane representing the imaging region is calculated as the target region.

For example, when the region of interest is expressed as labeled volume data, the target region calculation unit 7121 extracts points each corresponding to the foot of a perpendicular which extends from a point of the volume data to a plane representing the imaging plane and has a length within a predetermined threshold. A region corresponding to the convex closure of the extracted points serving as the feet of perpendiculars to the imaging region is obtained as the target region.

Figure 11:
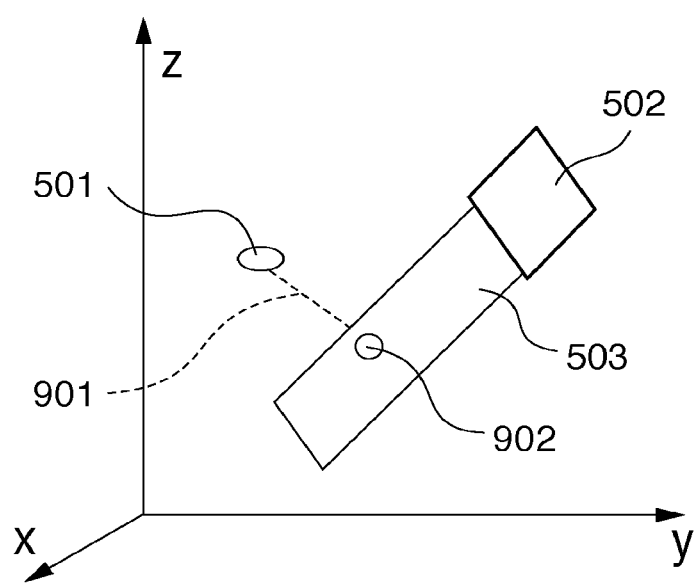
FIG. 11 is a view for explaining processing of obtaining a target region when a region of interest is a point.

If an intersection region is distinctly defined, the intersection region is preferably calculated as the target region. However, when the region of interest is a point, the frequency of generating an intersection region between the imaging region and the region of interest is sometimes low in a normal probe operation. In this case, as shown in FIG. 11, a perpendicular 901 is drawn from a region 501 of interest to an imaging region 503. A neighboring region 902 generated by a point on the imaging region 503, which corresponds to the foot of the perpendicular 901, is calculated as the target region. Using the neighboring region 902 as the target region allows to adjust the focus position of the ultrasonic diagnosis apparatus, like an intersection region 504.

More specifically, if the region of interest is a point, the region 501 of interest is a point of interest represented by three-dimensional coordinates. The target region calculation unit 7121 calculates a neighboring region corresponding to the point of interest. When the length of the perpendicular 901 drawn from the point of interest to the imaging region 503 is equal to or less than a predetermined threshold, the target region calculation unit 7121 calculates, as the neighboring region 902, a point serving as the foot of the perpendicular on the imaging region 503, and obtains the region (point) as the target region.

Note that the method of selecting a region to be obtained in the target region calculation is not limited to the above-described method. For example, an arbitrary method can be set such that if the intersection region between the region of interest and the imaging region exists, the intersection region is calculated as the target region, and if no intersection region exists, a neighboring region is calculated as the target region. Alternatively, the user may input an instruction to selectively use one of an intersection region and a neighboring region during the imaging operation.

The target region calculation unit 7121 sends information (target region information) representing the thus obtained target region to the parameter deciding unit 1022 of the succeeding stage. The target region calculation unit 7121 also sends the region information and the position and orientation information to the image generation unit 1031 of the succeeding stage.

In step S802, the target region calculation unit 7121 determines whether the target region could be obtained in step S801. Upon determining that the target region could not be obtained, the process returns to step S401, and the processes in steps S401, S402, and S801 are repeated based on the position and orientation information of the probe input at the next time. On the other hand, if the target region could be obtained, the process advances to step S803.

In step S803, the parameter deciding unit 1022 obtains an imaging parameter based on the target region information. The process in this step is almost the same as that in step S405. For example, independently for each scanning line, a near-side endpoint of a line segment where a scanning line overlap the target region is decided as a focus position. This enables to set a focus near the boundary of the region of interest especially when the target region is an intersection region.

Note that the focus position deciding method is not limited to this, as described in the first embodiment. For example, to image the entire interior of a wide region such as an organ before deciding an optimum focus position for a specific part, the distance up to the central point of the target region may be set as a focus position common to all scanning lines.

Finally, in step S408, the display unit 7132 displays the three-dimensional echogram (volume data) generated by the image generation unit 1031. For example, to compare the image with a cross-sectional image obtained by another modality, the display unit 7132 displays, based on a user instruction, the three-dimensional echogram as three cross sections that cross at right angles.

The volume data can be displayed by any method in accordance with the user's purpose. For example, when the user wants to observe a three-dimensional shape, volume rendering display may be designated. A MIP (Maximum Intensity Projection) image projected to each plane of a rectangular parallelepiped circumscribed by the volume data may be generated and displayed. ON/OFF of echogram display and the display method can be either set in the ultrasonic diagnosis apparatus in advance or switched during the imaging operation based on a user instruction.

If execution of the image display processing in step S408 is designated by a user instruction, the processes in steps S401 to S408 are repeated in accordance with the transmission rate. This allows the image generation unit 1031 to sequentially generate three-dimensional echograms with a focus set in the region of interest and the display unit 7132 to sequentially display the generated three-dimensional echograms during the imaging operation of the user.

Third Embodiment

In the second embodiment, a region of interest is designated by making the user directly input numerical values or based on volume data obtained from a three-dimensional image of another modality. In the third embodiment, a region of interest is set by a method different from that of the second embodiment. More specifically, the user operates the probe while observing an echogram obtained by an imaging unit 1100, and a region of interest is set based on a region designated by the user on an echogram of interest, unlike the second embodiment. This embodiment will be described below concerning only points different from the second embodiment.

<Arrangement of Ultrasonic Diagnosis Apparatus of Embodiment>

The arrangement of an ultrasonic diagnosis apparatus according to this embodiment is the same as in the second embodiment except the function of a region-of-interest acquisition unit 1010. Additionally, unlike the second embodiment, position and orientation information acquired by a position and orientation acquisition unit 1020 is also supplied to the region-of-interest acquisition unit 1010, and an echogram acquired by an echogram acquisition unit 1030 is also supplied to the region-of-interest acquisition unit 1010.

The region-of-interest acquisition unit 1010 collects information about a region (region of interest) designated by the user on an echogram supplied from the echogram acquisition unit 1030. Using the collected information and the position and orientation information supplied from the position and orientation acquisition unit 1020, the region-of-interest acquisition unit 1010 then obtains region information that defines the region of interest on the reference coordinate system.

<Processing Procedure to be Performed by Ultrasonic Diagnosis Apparatus>

Processing to be performed by the ultrasonic diagnosis apparatus according to the embodiment will be described next. The region-of-interest acquisition unit 1010 executes the following processing in step S301 of the flowchart of FIG. 3.

In step S301, the region-of-interest acquisition unit 1010 acquires an echogram of interest from the echogram acquisition unit 1030. This acquisition may be done based on, for example, an instruction input by the user. The region-of-interest acquisition unit 1010 causes a display unit 7132 to display the acquired echogram sequentially (as a live moving image). The user designates a region of interest while observing the echogram displayed on the display unit 7132. For example, the user fixes the probe at a morbid portion to display an echogram in which the morbid portion of interest is extracted. In this state, he/she then presses a predetermined key (to be referred to as a "still image acquisition key" hereinafter) of the keyboard. The region-of-interest acquisition unit 1010 causes the display unit 7132 to continuously display, as an echogram of interest, an echogram displayed on the display unit 7132 at the timing the user pressed the "still image acquisition key". In addition, the region-of-interest acquisition unit 1010 acquires, from the position and orientation acquisition unit 1020, the position and orientation information of the imaging unit 1100 when the echogram of interest was obtained, and stores it in a memory (not shown).

The region-of-interest acquisition unit 1010 also collects information about the region designated by the user on the echogram of interest. More specifically, the region-of-interest acquisition unit 1010 provides a GUI to be used by the user to designate a region of interest on the echogram of interest displayed on the display unit 7132, and collects information about the region of interest designated by the user. Based on the collected information and the position and orientation information supplied from the position and orientation acquisition unit 1020 at the timing the echogram of interest was obtained, the region-of-interest acquisition unit 1010 obtains region information that defines the region of interest on the reference coordinate system.

Note that to cause the user to designate a region on the echogram of interest, for example, a method of designating a circular region (the central point of a circle and an arbitrary point on the circumference) on the echogram is used. A sphere having the same center and radius as those of the designated circle is decided as the region of interest. Note that any other method is usable to designate a region on an image. A method of inputting a rectangle or a free shape as in a normal paint tool may be used. A point or a set of points on an image may be designated as a seed, and a result of automatic extraction of a region having image features similar to the points (or a circle that approximates the region) may be used. When a region on an image is designated using these methods, for example, an ellipsoid of revolution obtained by rotating the region about an appropriate axis or the product of ellipsoids of revolution about several axes is set as the region of interest on the reference coordinate system. Alternatively, a position of interest on the echogram of interest may be designated by a point, and the region of interest may be described as the position of the point on the reference coordinate system. Otherwise, regions may be designated on two or more echograms of interest by some method, and a three-dimensional region derived from these regions by view volume intersection may be obtained as the region of interest. The subsequent processes are the same as in the second embodiment.

As described above, according to this embodiment, the user can designate a region of interest while observing an echogram obtained by the probe at an arbitrary position and orientation. Especially, the user can designate a three-dimensional region on the reference coordinate system as the region of interest only by designating a two-dimensional region on a two-dimensional echogram. In addition, since the range of an image visualized in the imaging region can be designated as the region of interest by the same operation and display as in a normal ultrasonic diagnosis apparatus, the region-of-interest designation method is intuitively understandable for the user.

Fourth Embodiment

In the above-described embodiments, a point or a three-dimensional set of points on an object is designated as a region of interest. In this embodiment, the form of the region of interest is different from those in the above-described embodiments, and a cross section on an object is designated as a region of interest (cross section of interest). Particularly, this embodiment is characterized by designating, as a cross section of interest, an arbitrary cross section in a three-dimensional image acquired by another medical imaging apparatus (for example, MRI). This embodiment is also characterized by generating a high-quality echogram of the same cross section as the cross section of interest. Only points different from the second embodiment will be explained below.

<Arrangement of Ultrasonic Diagnosis Apparatus of Embodiment>

The arrangement of an ultrasonic diagnosis apparatus according to this embodiment is the same as in the second embodiment except that a region-of-interest acquisition unit 1010 acquires, as region information, information that defines a partial region of interest on a cross section in the reference coordinate system. The functions of a target region calculation unit 7121, parameter deciding unit 1022, and image generation unit 1031 are also different from those of the above embodiment to cope with the region of interest defined as a cross section. In addition, unlike the above-described embodiment, a display unit 7132 displays an echogram corresponding to a cross section of interest and information about a partial region of interest.

The region-of-interest acquisition unit 1010 acquires a three-dimensional image of an object obtained by an MRI or the like in advance, and causes the user to select one of a plurality of cross sections (tomograms) included in the acquired three-dimensional image. When the user selects one cross section (cross section of interest), information (cross-section-of-interest information) representing the selected cross section is generated. The cross-section-of-interest information is expressed by, for example, the coordinates and normal vector of one point on the cross section.

The region-of-interest acquisition unit 1010 also collects information (partial-region-of-interest information) representing a region (partial region of interest) designated by the user on the cross section of interest. Using the collected information and position and orientation information acquired by a position and orientation acquisition unit 1020, the region-of-interest acquisition unit 1010 generates region information that defines the partial region of interest on the reference coordinate system. The generated region information is stored in a region-of-interest information storage unit 1011, as in the above-described embodiments. On the other hand, the partial-region-of-interest information is sent to the display unit 7132. A more detailed description of the region-of-interest acquisition unit 1010 and a description of the target region calculation unit 7121, parameter deciding unit 1022, and image generation unit 1031 will be done later.

The display unit 7132 sequentially displays an echogram of the same cross section as the cross section of interest generated by the image generation unit 1031. The display unit 7132 also superimposes the information representing the partial region of interest on the echogram. The display unit 7132 will be described later in more detail.

<Processing Procedure to be Performed by Ultrasonic Diagnosis Apparatus>

Processing to be performed by the ultrasonic diagnosis apparatus according to the embodiment will be described next. Note that the practice procedure of this embodiment starts when a three-dimensional image of an object acquired by an MRI in advance is input to the region-of-interest acquisition unit 1010.

Figure 9:
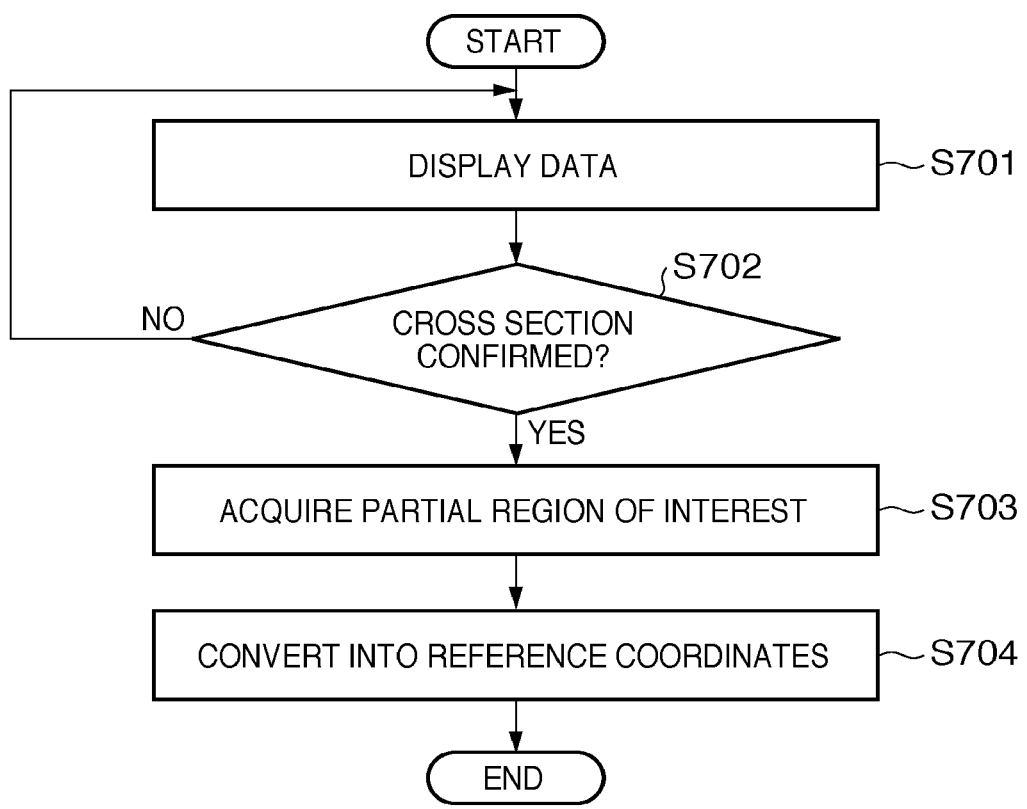
FIG. 9 is a flowchart illustrating details of a process in step S301.

The region-of-interest acquisition unit 1010 performs processing according to the flowchart of FIG. 3. However, in step S301, the region-of-interest acquisition unit 1010 performs processing according to the flowchart of FIG. 9. FIG. 9 is a flowchart illustrating details of the process in step S301.

In step S701, the region-of-interest acquisition unit 1010 displays, by volume rendering, a three-dimensional image acquired from an MRI on a GUI displayed on the display unit 7132. At this time, if a parameter to designate a cross section of interest in a subsequent process (the process of this step is executed even after step S702) has been set, the three-dimensional image is displayed by volume rendering while cutting out the cross section of interest. The image of the cross section of interest is also displayed as a two-dimensional image without parsing. The region-of-interest acquisition unit 1010 also displays a graphic operation object (for example, control point) to be used to receive a user instruction related to manipulation of the cross section. After ending the display, the region-of-interest acquisition unit 1010 waits for an instruction input from the user.

In step S702, the region-of-interest acquisition unit 1010 determines the user operation. Upon determining that the user has designated (updated) the cross section of interest by, for example, operating the displayed control point, the region-of-interest acquisition unit 1010 changes the parameter representing the cross section of interest, and returns the process to step S701. On the other hand, upon determining that an operation of confirming the cross section of interest has been input, the process advances to step S703.

In step S703, the region-of-interest acquisition unit 1010 receives a designation of a partial region of interest on the cross section of interest. The received designation, in other words, partial-region-of-interest information is sent to the display unit 7132. The partial region of interest is a partial region including a possible morbid or abnormal portion such as a cancerous tumor the operator wants to note on the cross section of interest (of which the operator wants to obtain an echogram). As the partial region of interest, for example, a circular, elliptic, rectangular, or other region is designated, based on an operation instruction from the user, on the two-dimensional image of the cross section of interest of the MRI displayed on the display unit 7132 in step S701. FIG. 12 is a view showing the relationship between volume data 1001, cross section 1002 of interest, morbid portion 1003, and partial region 1004 of interest of an MRI.

Note that as another method of designating the partial region of interest, the region-of-interest acquisition unit 1010 may acquire information about the position of a morbid region extracted automatically or manually by another means from the three-dimensional image of the MRI, and designate the partial region of interest based on the information. In this case, for example, a morbid region on the cross section 1002 of interest may directly be used as the partial-region-of-interest information. Alternatively, for example, an elliptic or rectangular region including a morbid region may be used as the partial-region-of-interest information.

Referring back to FIG. 9, in step S704, the region-of-interest acquisition unit 1010 converts the parameter representing the cross section of interest designated by the processes in steps S701 and S702 into a description based on the reference coordinate system. This allows to generate region information that defines the region of interest on the reference coordinate system. In step S302, the region information is stored in the region-of-interest information storage unit 1011.

Processing of generating a three-dimensional echogram with a focus on the cross section of interest will be described below with reference to FIG. 8 which shows the flowchart of the processing. Note that the processing of generating a three-dimensional echogram with a focus on the cross section of interest is implemented by making the following changes in the flowchart of FIG. 8.

Figure 10:
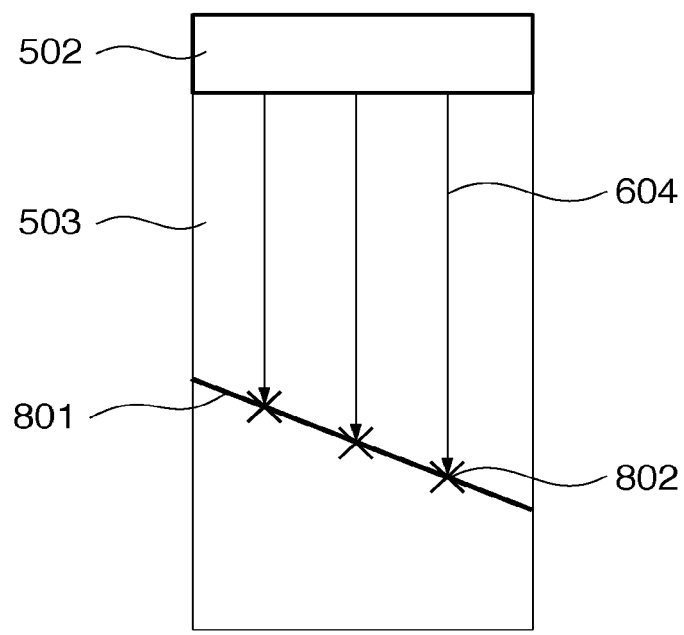
FIG. 10 is a view for explaining processes in steps S801 and S803.

Steps S401 and S402 are the same as in the second embodiment. In step S801, the target region is calculated based on the positional relationship between the imaging region and the region of interest, as in the second embodiment. In this embodiment, as shown in FIG. 10, an intersection region defined as a line 801 of intersection between a plane representing the region of interest and a plane representing the imaging region of the probe is calculated as the target region.

Step S802 is the same as in the second embodiment. In step S803, the parameter deciding unit 1022 decides the imaging parameter (the focus position of each scanning line) based on the target region obtained in step S801, as in the second embodiment. In this embodiment, as shown in FIG. 10, the intersection between each scanning line and the line 801 of intersection obtained in step S801 is set as the focus position of the scanning line. Step S406 is the same as in the second embodiment.

In step S407, the image generation unit 1031 stores echograms obtained by the imaging unit 1100, and integrates all echograms stored until this point of time, thereby generating an echogram of the cross section of interest (corresponding to the cross section of interest), as in the second embodiment. For example, as in the second embodiment, after a three-dimensional echogram is generated, an image is generated by cutting out the same cross section as the cross section of interest from the three-dimensional echogram using a known technique. Note that the image generation processing of this step is preferably high-speed processing that is repeatedly executable in accordance with the echogram transmission rate of the imaging unit 1100. Hence, as a suitable technique for the image generation processing, a three-dimensional echogram generated in the process of the step one cycle before is held and then updated using an echogram newly acquired in step S406.

Note that the method of generating the echogram of the cross section of interest is not limited to this. The image of the cross section of interest may be generated without intervening a three-dimensional echogram. For example, the values of pixels on the line 801 of intersection on each obtained echogram are sequentially plotted on an image to be generated, thereby generating a desired image without intervening a three-dimensional echogram.

In step S408, the display unit 7132 displays the echogram of the cross section of interest generated in step S407. Additionally, as shown in FIG. 13, an indicator (a dotted circle in FIG. 13) that points out the position of the partial region 1004 of interest is displayed on an image 1101 of the cross section of interest. Note that this image is preferably displayed by the side of the image of the cross section of interest of the MRI, as in step S701. Especially, when images of two modalities are displayed at the same magnification, the user can easily grasp the correspondence between the modalities.

Note that the image display form in step S408 is not limited to the above-described one. For example, MRI volume rendering may be performed as in step S701, and the generated echogram may be superimposed on (or replaced with) the portion of the cross section of interest. A frame (wireframe) or plane representing the imaging region of the echogram may be displayed on the same coordinate system as that of the volume rendering. The echogram acquired in step S406 may be displayed (for example, semitransparently) in the imaging region. Such display facilitates to grasp the positional relationship between the cross section of interest and the probe. Note that the display form to be used in step S408 is preferably selectable based on an instruction input by the user.

As shown in FIG. 14, the display unit 7132 can display, in accordance with an instruction input by the user, a high-quality region 1201 in the image 1101 of the cross section of interest distinguishably in a tone of color or luminance different from other regions. The high-quality region 1201 is, for example, a region formed from pixels which are generated using echograms equal to or more than a threshold when generating the pixels of the image of the cross section of interest using obtained echograms. As is generally known, when reconstructing an image using a plurality of echograms, the image quality rises as the number of echograms used increases. Also, the high-quality region is a region on the cross section of interest formed from pixels each having a distance from a focus position equal to or less than a predetermined threshold in an obtained echogram. A pixel having a predetermined distance or less from a focus position is obtained more accurately than a pixel far apart more than the predetermined distance. Hence, a region reconstructed from such pixels has image quality higher than that of other regions.

The above-described processing is repeated in accordance with the echogram transmission rate of the imaging unit 1100. As a result, when the user changes the position and orientation of the probe by the same operation as in normal diagnosis, echogram imaging is repeated, and an imaging parameter appropriate for observing the cross section of interest is set independently of the position and orientation of the probe (that is, focus processing is always performed for the cross section of interest). Integrating the images enables to generate a high-quality echogram of the cross section having a focus on the cross section of interest.

When the above-described processing is repeated in accordance with the transmission rate, the echograms of the cross section of interest are sequentially generated during the user's imaging operation, and the generated echograms (at that point of time) are sequentially displayed. This allows the user to determine whether imaging is sufficient or whether the imaging position is appropriate while visually observing a target echogram. In addition, superimposing information about the position of the partial region of interest allows the user to confirm, at a glance, the position of a morbid portion (to be imaged by ultrasonic waves) visualized on the cross section of interest of the MRI or whether the image at that portion has been generated. It is consequently possible to efficiently acquire desired echograms. The above-described procedure makes it possible to obtain a high-quality echogram corresponding to the cross section of interest of the MRI by an efficient operation.

Note that in this embodiment, the processes in steps S407 and S408 are executed for each acquired frame. However, the processes need not always be executed for each acquired frame. For example, if the processes in steps S407 and S408 cannot be done in a full frame, they may be executed in the background for every several frames. Alternatively, the processes in steps S407 and S408 may be executed after imaging processing in steps S401 to S406 has been executed for sufficient frames.

Note that in this embodiment, a two-dimensional image has been exemplified as the partial region of interest on the cross section of interest. However, the embodiment can also be practiced for a partial region of interest in a three-dimensional region of interest.

<First Modification>

In the above-described embodiment, an imaging parameter is decided, and the imaging unit 1100 is controlled using the decided imaging parameter. However, the decided imaging parameter may be set manually by the user. In this case, an information processing unit 7100 displays the decided imaging parameter on the display unit 7132. The user views the display, and manually sets the displayed imaging parameter in the imaging unit 1100.

<Second Modification>

In the above embodiment, an ultrasonic diagnosis apparatus for measuring an ultrasonic echo has been described as an example of an image diagnosis apparatus. However, the image diagnosis apparatus may be another modality. For example, the image diagnosis apparatus may be a PAT (Photo-Acoustic Tomography) apparatus which images an object using a probe having a laser beam source and an ultrasonic probe for reception. In this case, for example, the laser intensity can be adjusted as the imaging parameter in accordance with the position of the target region on the imaging region. Note that the above-described various embodiments and modifications may be combined as needed.

Fifth Embodiment

In the above-described embodiments, all of the units included in the information processing unit 1000 shown in FIG. 1 and the units included in the information processing unit 7100 shown in FIG. 7 are formed from hardware. However, the region-of-interest information storage unit 1011 may be implemented by a memory, the display unit 7132 by a monitor, and the remaining units by computer programs. In this case, a computer including the region-ofinterest information storage unit 1011 as a memory, the display unit 7132 as a monitor, and a CPU for executing the remaining units as computer programs functions as the information processing unit 1000 or 7100.

Figure 2:
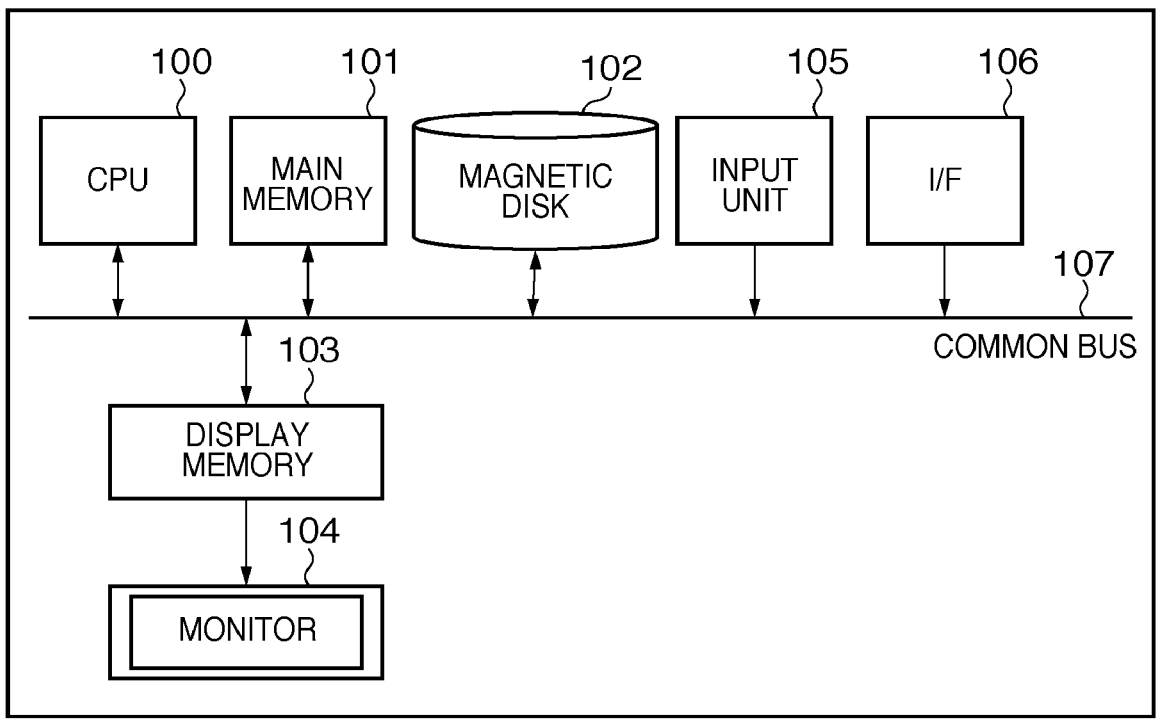
FIG. 2 is a block diagram showing an example of the hardware configuration of a computer applicable to an information processing unit 1000 or 7100.

FIG. 2 is a block diagram showing an example of the hardware configuration of a computer applicable to the information processing unit 1000 or 7100.

A CPU 100 controls the entire computer using computer programs and data stored in a main memory 101, and also executes the above-described processing of the information processing unit 1000 or 7100.

The main memory 101 has an area for temporarily storing computer programs and data loaded from a magnetic disk 102, data received from an external device via an I/F (interface) 106, and the like. The main memory 101 also has a work area to be used by the CPU 100 to execute various kinds of processing. That is, the main memory 101 can provide various kinds of areas as needed. The main memory 101 also functions as, for example, the region-of-interest information storage unit 1011.

The magnetic disk 102 is a mass information storage device functioning as a hard disk drive. The magnetic disk 102 stores the OS (Operating System), and computer programs and data to cause the CPU 100 to execute the functions of units other than the region-of-interest information storage unit 1011 and the display unit 7132 in FIGS. 1 and 7. The data include known data described above and process target data. The computer programs and data stored in the magnetic disk 102 are loaded to the main memory 101 as needed under the control of the CPU 100, and processed by the CPU 100.

An input unit 105 is formed from a keyboard and a mouse which the user can operate to input various instructions and data. All instructions and data input by the user in the above explanation are input by causing the user to operate the input unit 105.

The I/F 106 connects the position and orientation measuring unit 1200 and the imaging unit 1100 to the computer, and is formed from IEEE1394, USB, Ethernet® port, or the like. The computer performs data communication with the position and orientation measuring unit 1200 and the imaging unit 1100 via the I/F 106.

A display memory 103 temporarily stores data of a screen to be displayed on a monitor 104. The monitor 104 displays a screen based on the screen data stored in the display memory 103.

The monitor 104 is formed from a CRT or a liquid crystal display so as to display the processing result of the CPU 100 as an image or characters. The monitor 104 functions as the display unit 7132. A bus 107 connects the above-described units.

Note that the arrangement of an apparatus applicable to the information processing unit 1000 or 7100 is not limited to that shown in FIG. 2. Any other arrangement is usable if it can implement the functional arrangement shown in FIG. 1 or 7.

Other Embodiments

The present invention is also achieved by executing the following processing. Software (program) which implements the functions of the above-described embodiments is supplied to a system or apparatus via a network or various kinds of storage media. The computer (or CPU or MPU) of the system or apparatus reads out and executes the program.

The present invention is not limited to the above embodiments, and various changes and modifications can be made within the spirit and scope of the present invention. Therefore, to apprise the public of the scope of the present invention, the following claims are appended.

This application claims the benefit of Japanese Patent Application No. 2009-112294, filed May 1, 2009, which is hereby incorporated by reference herein in its entirety.

The invention claimed is:

1. A system for acquiring an echogram of an object, comprising:
   an ultrasonic probe;
   a memory storing a program; and
   one or more processors which, by executing the program, function as:
      a first acquisition unit configured to acquire region information that defines a region of interest on the object;
      a second acquisition unit configured to acquire position and orientation information representing a position and orientation of the ultrasonic probe;
      a third acquisition unit configured to acquire an intersection region between an imaging range of the ultrasonic probe and the region of interest defined by the acquired region information using the acquired position and orientation information; and
      a control unit configured to control a focus of an ultrasonic wave transmitted from the ultrasonic probe to set the focus to a first region corresponding to the intersection region in a case where the third acquisition unit acquires the intersection region between the imaging range of the ultrasonic probe and the region of interest,
   wherein the control unit controls the focus of the ultrasonic wave transmitted from the ultrasonic probe to set the focus to a second region vertically projected from the region of interest to the imaging range in a case where the third acquisition unit cannot acquire the intersection region between the imaging range of the ultrasonic probe and the region of interest, and
   wherein the acquisition of the position and orientation information, the acquisition of the intersection region, and the control of the focus of the ultrasonic wave transmitted from the ultrasonic probe are repeatedly performed.

2. The system according to claim 1, wherein the acquisition of the position and orientation information, the acquisition of the intersection region, and the control of the focus of the ultrasonic wave transmitted from the ultrasonic probe are repeatedly performed based on a transmission interval of an echogram by an image capturing unit including the ultrasonic probe.

3. The system according to claim 1, wherein the third acquisition unit acquires the intersection region on a surface of the region of interest.

4. The system according to claim 1, wherein the third acquisition unit acquires the intersection region from an interior of the region of interest.

5. The system according to claim 1, wherein the third acquisition unit acquires the intersection region for each scanning line of an echogram transmitted from the ultrasonic probe.

6. The system according to claim 1, wherein the second acquisition unit acquires the imaging range of an echogram based on the position and orientation information, the third acquisition unit acquires the intersection region between the imaging range acquired by the second acquisition unit and the region of interest defined by the acquired region information.

7. The system according to claim 1, wherein the control unit delays the ultrasonic wave transmitted from the ultrasonic probe to control a focus of the ultrasonic wave transmitted from the ultrasonic probe.

8. The system according to claim 1, wherein the first acquisition unit acquires the region information based on an image obtained by a modality other than an ultrasonic diagnosis apparatus.

9. The system according to claim 8, wherein the image obtained by the modality other than the ultrasonic diagnosis apparatus includes an MRI image or a PET image.

10. The system according to claim 1, wherein the control unit calculates a focus position at which an in-focus state is obtained in a region on the object corresponding to the intersection region.

11. The system according to claim 1, wherein the first acquisition unit acquires the region information that defines the region of interest on volume data which has been acquired by an apparatus other than an ultrasonic diagnosis apparatus.

\* \* \* \* \*